United States Patent
Hamamatsu et al.

(10) Patent No.: US 7,417,723 B2
(45) Date of Patent: *Aug. 26, 2008

(54) METHOD OF INSPECTING A SEMICONDUCTOR DEVICE AND AN APPARATUS THEREOF

(75) Inventors: Akira Hamamatsu, Yokohama (JP); Minori Noguchi, Mitsukaido (JP); Yoshimasa Ohshima, Yokohama (JP); Hidetoshi Nishiyama, Fujisawa (JP); Kenji Oka, Hitachinaka (JP); Takanori Ninomiya, Hiratsuka (JP); Maki Tanaka, Yokohama (JP); Kenji Watanabe, Oume (JP); Tetsuya Watanabe, Honjyou (JP); Yoshio Morishige, Honjyou (JP)

(73) Assignees: Hitachi, Ltd., Tokyo (JP); Hitachi High-Technologies Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 11/443,222

(22) Filed: May 31, 2006

(65) Prior Publication Data

US 2006/0215153 A1 Sep. 28, 2006

Related U.S. Application Data

(63) Continuation of application No. 11/117,336, filed on Apr. 29, 2005, now Pat. No. 7,061,602, which is a continuation of application No. 09/791,682, filed on Feb. 26, 2001, now Pat. No. 6,888,959.

(30) Foreign Application Priority Data

Mar. 2, 2000 (JP) ............................. 2000-061836

(51) Int. Cl.
*G01N 21/00* (2006.01)
*G06K 9/00* (2006.01)

(52) U.S. Cl. .................. 356/237.2; 356/237.5; 382/149; 382/224

(58) Field of Classification Search ... 356/237.1–237.5, 356/394; 382/149, 224; 250/559.41, 559.39, 250/559.45
See application file for complete search history.

(56) References Cited

U.S. PATENT DOCUMENTS

| | | | |
|---|---|---|---|
| 5,986,263 A | 11/1999 | Hiroi et al. | |
| 6,002,989 A | 12/1999 | Shiba et al. | |
| 6,010,405 A | 1/2000 | Morawiec | |
| 6,307,550 B1 | 10/2001 | Chen et al. | |
| 6,583,414 B2 | 6/2003 | Nozoe et al. | |
| 6,882,793 B1 | 4/2005 | Fu et al. | |
| 6,888,959 B2 | 5/2005 | Hamamatsu et al. | |
| 7,061,602 B2 * | 6/2006 | Hamamatsu et al. ..... | 356/237.2 |

* cited by examiner

*Primary Examiner*—Hoa Q Pham
(74) *Attorney, Agent, or Firm*—Antonelli, Terry, Stout & Kraus, LLP.

(57) ABSTRACT

A method and apparatus of inspecting a sample, in which the sample is inspected under a plurality of inspection conditions, and inspection data obtained by inspecting the sample under each of the plurality of inspection conditions and position information on the sample of the inspection date in correspondence with the respective inspection conditions, are stored. The inspection data for each of the plurality of inspection conditions is against each other by the use of the position information on the sample to determine a position to be inspected in detail, and an image of the sample at a position to be inspected in detail is obtained. The obtained image is classified, the inspection condition of the sample by the use of information of classification of the image is determined.

12 Claims, 14 Drawing Sheets

FIG. 6
INSPECTION APPARATUS A
INSPECTION CONDITION Ta
INSPECTION APPARATUS A
INSPECTION CONDITION Tb
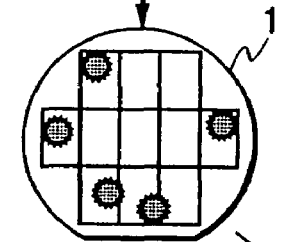
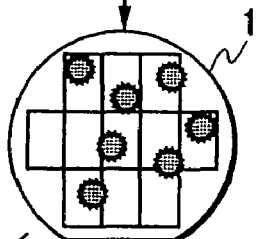
INSPECTION DATA DaTa
INSPECTION DATA DaTb
IDENTITY JUDGMENT ~30
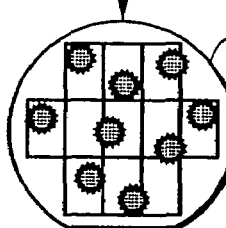
DATA AFTER IDENTITY JUDGMENT
REVIEW ~40
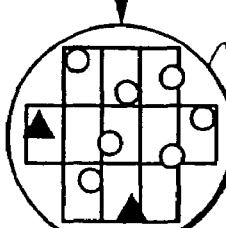
○: FOREIGN SUBSTANCE
▲: FALSE INFORMATION
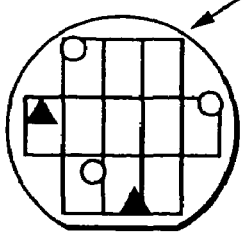
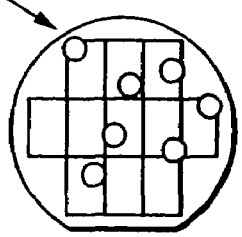
INSPECTION DATA KaTa
INSPECTION DATA KaTb INSPECTION DATA DaTa INSPECTION DATA DaTb

LOGICAL OR DATA

IDENTITY DATA

NON-IDENTITY DATA

INSPECTION DATA DaTa

INSPECTION DATA ONLY UNDER INSPECTION CONDITION Tb

▲ COMMON DETECTED SUBSTANCE
○ DETECTED UNDER CONDITION Ta
□ DETECTED UNDER CONDITION Tb

FIG. 10(a)    FIG. 10(b)
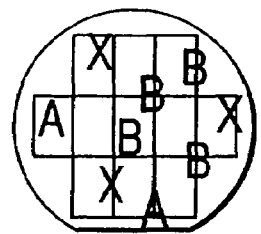
DISPLAY BY
CHARACTER
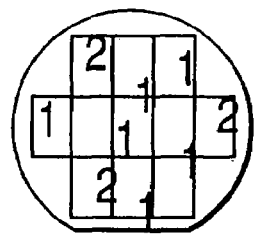
DISPLAY BY
NUMERAL
FIG. 11
| INSPECTION CONDITION | CONDITION ITEM | | | REVIEW RESULT | | | NOT-YET-REVIEWED | THRESHOLD IMAGE/ THRESHOLD HISTOGRAM |
|---|---|---|---|---|---|---|---|---|
| | THRESHOLD | SPATIAL FILTER | LASER POWER | FALSE INFORMATION | FOREIGN SUBSTANCE | SCRATCH AND DEFECT | | |
| Ta | 100 | 5 | 100mW | 4 | 100 | 5 | | |
| Tb | | | | 2 | 50 | 10 | | |
| Tc | | | | 0 | 10 | 8 | | |
| Td | | | | 10 | 5 | 2 | | |
| TaUTbUTcUTd (COMMON) | | | | 15 | 74 | 7 | | |

METHOD OF INSPECTING A SEMICONDUCTOR DEVICE AND AN APPARATUS THEREOF

CROSS REFERENCE TO RELATED APPLICATION

This application is a continuation of U.S. application Ser. No. 11/117,336, filed Apr. 29, 2005 now U.S. Pat. No. 7,061,602, which is a continuation of U.S. application Ser. No. 09/791,682, filed Feb. 26, 2001, now U.S. Pat. No. 6,888,959, the contents of which are incorporated herein by reference.

BACKGROUND OF THE INVENTION

1. Field of the Invention

The present invention relates to a method of inspecting a semiconductor device by which an inspection can be performed under proper inspection conditions on a semiconductor substrate manufactured in a desired manufacturing process of a semiconductor device and an apparatus thereof and, more particularly, to a method of finding an inspection condition in an inspection apparatus, by which a proper inspection condition is selected to a sample to be inspected and a method of selecting an inspection apparatus to a sample to be inspected.

2. Description of the Related Art

An inspection condition in an inspection apparatus have been conventionally determined by the steps: inspecting a sample for calibration, which has bumps and dips equivalent to actual foreign particles and defects, under a certain inspection condition; analyzing the state of detection of the bumps and dips; in the case where the results of the analysis are not good, inspecting the sample for calibration again under a changed inspection conditions; and the inspection of the sample and analyzing the state of detection of the bumps and dips; and repeating these procedures under different inspection conditions until the results of analysis become satisfactory. In this way, a proper inspection condition 1 is set.

Here, in Japanese Unexamined Patent Publication No. 9-306957 (related art 1) is disclosed a technology for making an identity judgment on a foreign substance in a plurality of processes of a semiconductor wafer.

Also, in Japanese Unexamined Patent Publication No. 4-106460 (related art 2) is disclosed a defect detecting technology for calculating the quantity of feature of the same image to be inspected by two different kinds of parameters, identifying objective defects, detecting defects identified in common by two kinds of parameters to thereby eliminate the duplication of detection of the defects.

In this connection, since a circuit pattern formed on a semiconductor device is becoming more microscopic, foreign particles, circuit pattern defects, and scratches which are required to be detected by inspection are growing more microscopic.

Further, a semiconductor is manufactured through a very large number of manufacturing processes. Therefore, an inspection apparatus needs to be applied to a semiconductor wafer manufactured through various manufacturing processes. However, the condition of the surface (underlying layer) of the semiconductor wafer manufactured through various manufacturing processes varies variously. In this manner, the inspection apparatus needs to detect particles to be detected such as foreign particles, circuit pattern defects, and the scratches, which are growing more microscopic, from the variously changing surface of the semiconductor wafer. Therefore, it is necessary to optimize subtle inspection conditions.

However, it is difficult to form bumps and dips equivalent to foreign particles and defects on the surface having variously changing conditions as a test sample for calibration and hence the above-mentioned related arts have a problem that it is difficult to set a proper inspection condition by the use of a test sample for calibration.

SUMMARY OF THE INVENTION

The present invention provides an inspection method for solving the above-mentioned problem and capable of inspecting particles to be detected, such as foreign particles, in accordance with the condition of the surface of a sample to be inspected which is manufactured in various manufacturing processes, and an apparatus thereof.

That is, the present invention provides a method of inspecting a sample, the method comprising the steps of: inspecting the sample under a plurality of inspection conditions; storing inspection data obtained by inspecting the sample under each of the plurality of inspection conditions and the position information on the sample of the inspection date in correspondence with the respective inspection conditions; checking the inspection data for each of the plurality of inspection conditions against each other by the use of the position information on the sample to determine a position to be inspected in detail; obtaining the image of the position to be inspected in detail; classifying the obtained image; and determining the inspection condition of the sample by the use of the information of classification of the image.

Further, the present invention provides a method of inspecting a sample, the method comprising the steps of: inspecting the sample under a plurality of inspection conditions; storing inspection data obtained by inspecting the sample under each of the plurality of inspection conditions and the position information on the sample of the inspection date in correspondence with the respective inspection conditions; checking the inspection data for each of the plurality of inspection conditions against each other by the use of the position information of the inspection date on the sample to determine a position to be inspected in detail; obtaining the image of the position to be inspected in detail; classifying the obtained image; making a group of inspection data by the use of the information of classification of the image and the inspection condition corresponding to the image, and displaying the group of inspection data on a screen; and determining the inspection condition of the sample out of the group of inspection data displayed on the screen.

Still further, the present invention provides a method of inspecting a sample, the method comprising the steps of: inspecting the sample under a plurality of inspection conditions and storing the information of a candidate for a position to be observed in detail under each of the plurality of inspection conditions; determining a position to be inspected in detail out of the stored information of the candidate for the position to be inspected in detail under each of the plurality of inspection conditions; obtaining the image of the position to be inspected in detail; determining the inspection condition of the sample by the use of the obtained information of the image; and inspecting the sample under the determined inspection condition.

Also, according to the present invention, an apparatus for inspecting a sample is constituted by: inspection means for inspecting the sample under a set inspection condition; inspection condition setting means for setting the inspection condition of the inspection means; storage means for storing the position data of a candidate to be inspected in detail of the sample, which are obtained by sequentially inspecting the sample under a plurality of inspection conditions set by the inspection condition setting means with the inspection means, in correspondence with the data of the plurality of inspection conditions; checking means for checking the position data of the candidate to be inspected in detail, which are stored in the storage means, against each other for each of the plurality of inspection conditions to determine a position to be inspected in detail; detailed image obtaining means for obtaining the image of the position to be inspected in detail, which is determined with the checking means; image classifying means for classifying the image obtained with the detailed image obtaining means; and inspection condition determining means for determining the inspection condition of the sample by the use of the information of the image classified by the image classifying means.

Also, according to the present invention, an apparatus for inspecting a sample is constituted by: inspection means for inspecting the sample under a plurality of inspection conditions; storage means for storing inspection data obtained by inspecting the sample under each of the plurality of inspection conditions with the inspection means and the position information on the sample of the inspection date in correspondence with the respective inspection conditions; detailed inspection position determining means for checking the inspection data, which are stored in the storage means, for each of the plurality of inspection conditions against each other by the use of the position information on the sample to determine a position to be inspected in detail; detailed inspection image obtaining means for obtaining the image of the position to be inspected in detail which is determined with the detailed inspection position determining means; classification means for classifying the image obtained with the detailed inspection image obtaining means; inspection data making means for making a group of inspection data by the use of the information of classification of the image classified with the classification means and the inspection condition corresponding to the image, and displaying the group of inspection date on a screen; and selection means for selecting the inspection condition of the sample out of the group of inspection data displayed on the screen with the inspection data making means.

Also, according to the present invention, an apparatus for inspecting a sample is constituted by: inspection means for inspecting the sample under a plurality of inspection conditions and storing the information of a candidate of a position to be observed in detail for each of the plurality of inspection conditions; detailed inspection position determining means for determining a position to be inspected in detail out of the candidates of the positions to be inspected in detail, which are stored in the inspection means, under each of the plurality of inspection conditions; detailed image obtaining means for obtaining the image of the position to be inspected in detail which is determined with the detailed inspection position determining means; and inspection condition determining means for determining the inspection condition of the sample by the use of the information of the image obtained with the detailed image obtaining means.

These and other objects, features and advantages of the invention will be apparent from the following more particular description of preferred embodiments of the invention, as illustrated in the accompanying drawings.

BRIEF DESCRIPTION OF THE DRAWINGS

FIG. 6 is an illustration to show a first example of a processing flow for selecting an optimal inspection condition to a sample to be inspected, in accordance with the present invention.

FIG. 10 is an illustration to show examples of check data displayed by characters or numerals.

FIG. 11 is an illustration to show an embodiment in which inspection data including the data assigned by classifying a detected substance for the respective inspection conditions are displayed in the form of a list.

FIG. 13 is an illustration to show the results of analysis of the materials of foreign particles and the like.

DESCRIPTION OF THE PREFERRED EMBODIMENTS

Preferred embodiments of an inspection method and an apparatus thereof in accordance with the present invention will be described with reference to the accompanying drawings.

To begin with, a case where a sample to be inspected is a semiconductor wafer will be described.

Since a semiconductor device is manufactured by many manufacturing processes, a semiconductor wafer is different in the material of a surface and the shape of a circuit pattern between the manufacturing processes. Also, a foreign substance inspection apparatus or an appearance inspection apparatus is used over a plurality of different manufacturing processes, or is provided in each of a plurality of different manufacturing processes. As a result, the present invention provides a method capable of inspecting a semiconductor wafer by adjusting inspection conditions and setting an optimal inspection condition for each manufacturing process, and an apparatus thereof.

Also, a foreign substance, a circuit pattern defect, and a flaw like a scratch, which are permissible on a semiconductor wafer, are becoming increasingly microscopic. For this reason, the present invention is intended to assign a manufacturing process a suitable inspection apparatus among the inspection apparatuses of the same kind having a slight difference in performance among them. Further, even in the case where different kinds of inspection apparatuses are used, they are different in an inspection capacity among them and hence the present invention is intended to assign a suitable kind of inspection apparatus to a manufacturing process.

Figure 1:
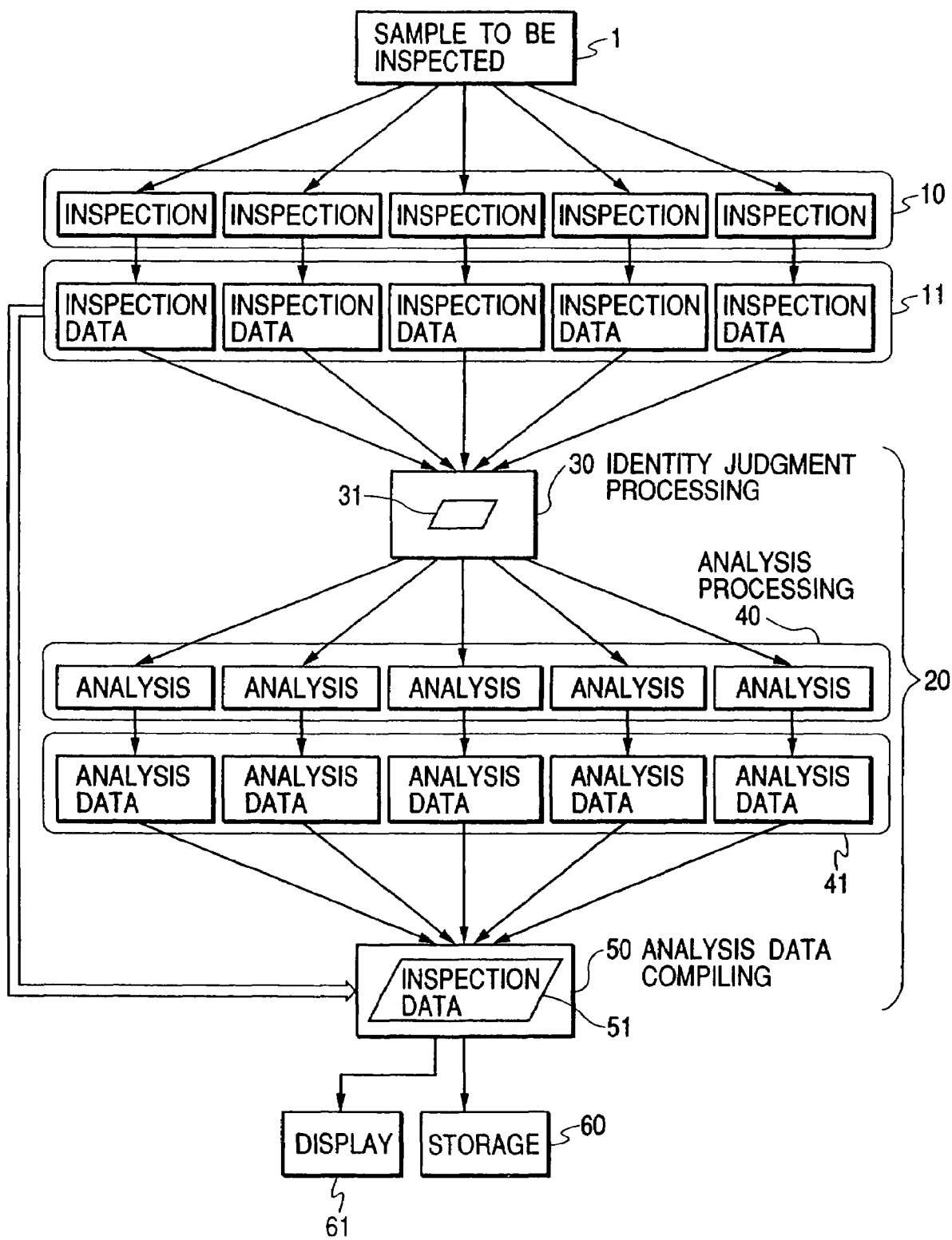
FIG. 1 is an illustration of a schematic functional configuration and a schematic processing flow to show one preferred embodiment of an inspection apparatus or a system thereof in accordance with the present invention.

Next, examples of an inspection method and an apparatus thereof in accordance with the present invention will be described with reference to FIG. 1.

In a group 10 of a plurality of kinds of inspections, a plurality of kinds of inspections are performed on foreign particles and defects (for example, microscopic uneven defects including defects of a circuit pattern, defects, and the like) on a sample to be inspected 1 such as semiconductor wafer. This group 10 of inspections includes the following inspection processes: (a) inspections are performed on the sample under a plurality of different inspection conditions of illuminating condition, detecting condition, image processing condition (condition of inspection algorithm), and the like by the use of the same inspection apparatus; (b) inspections are performed on the sample by the use of a plurality of inspection apparatuses of the same kind or approximately the same kind; (c) inspections are performed on the sample by the use of inspection apparatuses of different kinds (for example, an optical inspection apparatus shown in FIG. 2, an optical inspection apparatus shown in FIG. 3, an optical inspection apparatus shown in FIG. 4, or a SEM appearance inspection apparatus).

A group of inspection data 11 is obtained as a set as the results of inspections from the respective inspections in the group 10 of plural kinds of inspections performed on a sample to be inspected having a surface condition made by a certain manufacturing process.

Further, in a CPU 20, an identity judgment processing (check processing) 30 is performed on the group of inspection data 11 obtained by the plural kinds of inspections conducted in the group 10 of inspections, and the results of the identity judgment processing 30 (results of the check processing) are taken out as data 31 after the identity judgment processing (results of the check processing), and an analysis processing 40 is performed on the data. In this manner, the identity judgment processing 30 performed on the group of inspection data 11 largely decreases the number of detected particles in the data 31 after the identity judgment processing 30 by the number of data judged to be identical. In the analysis processing 40, the detected particles, largely decreased in number, are analyzed (reviewed) in detail by various kinds of analysis processes and are classified by category (for example, foreign substance, false information, circuit pattern defect, scratch (flaw), and the like) to produce a group 41 of analysis data. Naturally, sensitivity (size of foreign substance, circuit pattern defect and scratch) is also included in the category of classification and, for example, the sensitivity of the foreign substance includes a detection capability of 0.1 μm, 0.2 μm, and 0.5 μm.

In an analysis data compiling 50, the information of the group 41 of analysis data (classification of detected particles by category) obtained by the analysis processing 40 is fed back to the group of inspection data 11 and the results thereof can be stored as a single unit in a storage device 60 as inspection data 51 and also displayed on a display device 61. That is, in the analysis data compiling 50, by feeding back the information of the group 41 of analysis data (classification of detected particles by category) to the data obtained from the group of inspection data 11, a group of inspection data 51$a$ can be produced as the inspection data 51, for example, a group 51$a$ of inspection data shown in FIG. 5.

By displaying the group 51$a$ of inspection data, for example, on the display device unit 61, an operator can select, on a display screen, an optimal inspection condition for the sample 1 to be inspected among the group 10 of plural kinds of inspections and can set the selected inspection condition for an inspection apparatus. As a result, the inspection apparatus can perform an inspection on the sample 1 to be inspected under the set optimal inspection condition.

As described above, according to the present invention, the group 10 of plural kinds of inspections are performed on the sample to be inspected which has a certain surface condition manufactured by a given manufacturing process to produce, in a single unit, the group 11 of inspection data as the results of the respective inspections; and the identity judgment processing (check processing) 30 is preformed on these produced group 11 of inspection data to produce the data 31 to reduce the number of detected particles on which the analysis processing (reviewing) 40 is performed; and the analysis processing (reviewing) 40 is performed on the reduced number of detected particles to classify the detected particles by category or kind; and the classified kinds of the detected particles are fed back to the group 11 of inspection data. In this way, the operator can select an optimal inspection condition among the plural kinds of inspections and set the optimal condition to the inspection apparatus with efficiency in a short time. Of course, it is possible to instantaneously recognize the distribution of the detected particles on the sample to be inspected by displaying the data after the identity judgment processing.

Figure 2:
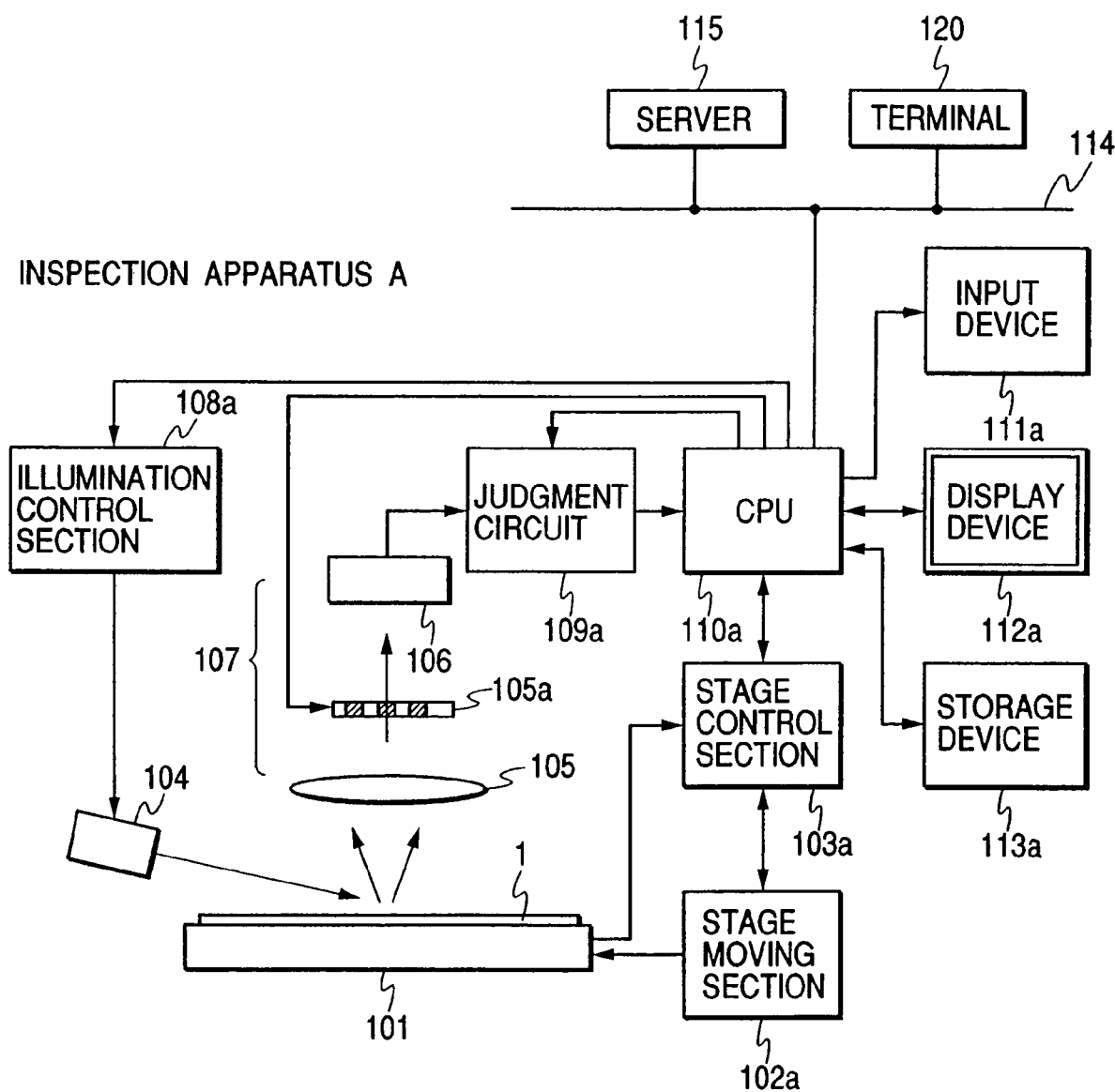
FIG. 2 is a schematic block diagram showing an example of an inspection apparatus A for inspecting foreign particles and the like, in accordance with the present invention.

As an example of an inspection apparatus A for inspecting a foreign substance, there is provided an apparatus having a configuration shown in FIG. 2. That is, the apparatus is composed of: a stage 101 for having a sample 1 to be inspected 1 placed thereon and measuring its displacement coordinates; a stage moving section 102$a$ for moving the stage 101; a stage control section 103$a$ for controlling the stage moving section 102$a$ based on the displacement coordinates of the stage 101 measured by the stage 101; an obliquely illuminating optical system 104 for obliquely illuminating the sample 1 to be inspected, which is placed on the stage 101; a detecting optical system 107 including a collective lens 105 for collecting scattering light (diffracted light of low order other than 0 order) from the surface of the sample 1 to be inspected and a photoelectric transducer 106 composed of a TDI, a CCD sensor or the like; an illumination control section 108 for controlling the quantity of illuminance and the angle of irradiation when light from the obliquely illuminating optical system 104 illuminates the sample 1 to be inspected; a judgment circuit (inspection algorithm circuit) 109a which aligns an inspection image signal produced by the photoelectric transducer 106 with a standard image signal (reference image signal) produced by a neighboring chip or cell, and compares them to extract a differential image from both the image signals, and judges the extracted differential image by a previously predetermined threshold to detect an image signal indicating a foreign substance to judge the foreign substance or, if necessary, further calculates the quantity of features (area, length, center of gravity, and the like) of the detected image signal indicating the foreign substance to judge the foreign substance; a CPU 110a for performing various kinds of processes on the foreign substance judged by the judgment circuit 109a based on the stage coordinate system obtained by the stage control section 103a; an input/output device 111a (key board, mouse, recording media, or the like) connected to the CPU 110a; a display device 112a; and a storage device 113a for storing various kinds of inspection data processed by the CPU 110a.

The above-mentioned inspection apparatus A detects scattering light (diffracted light of low order), which is generated by a foreign substance existing on the sample 1 to be inspected when light is obliquely applied to the sample 1 to be inspected by the obliquely illuminating optical system 104, by the detecting optical system 107.

Figure 5:
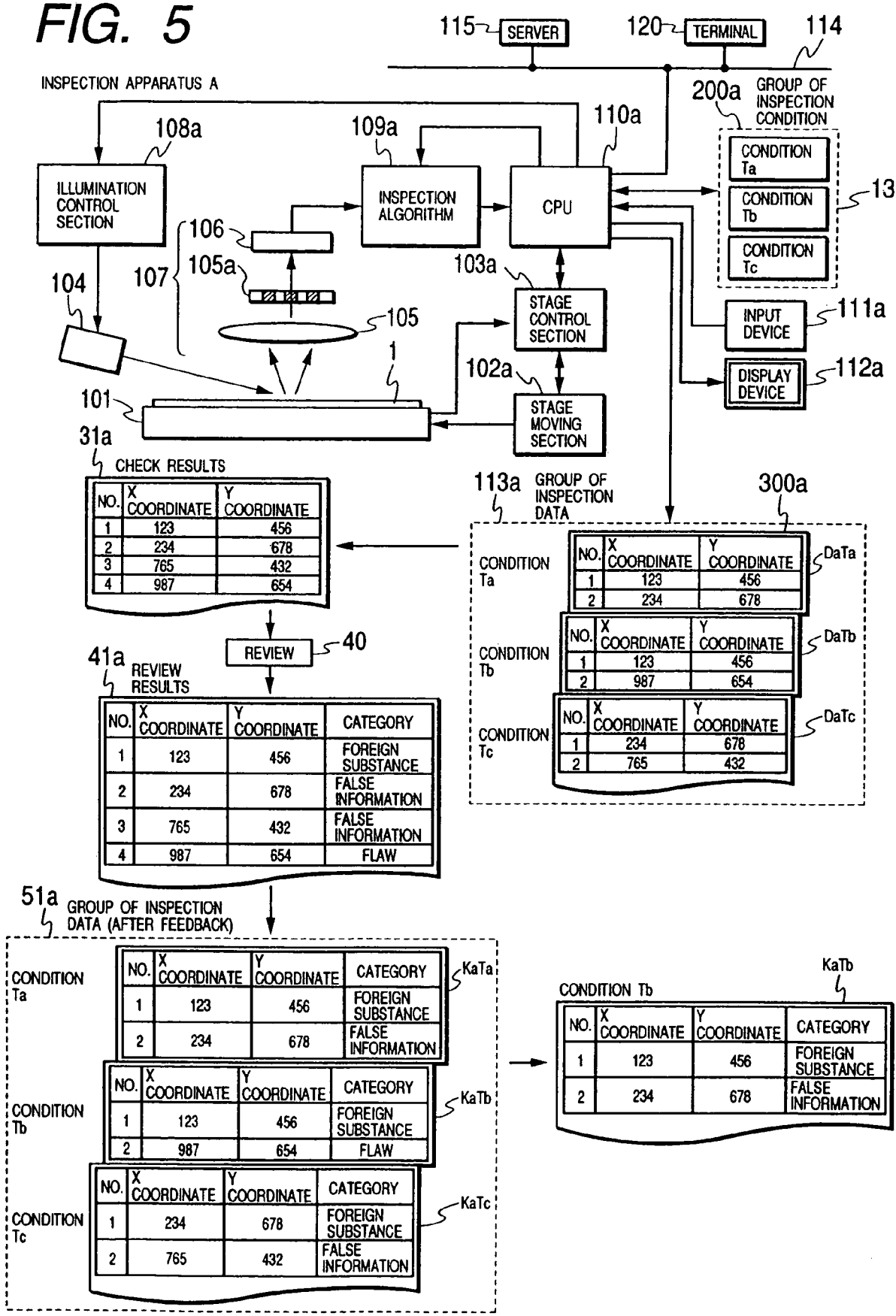
FIG. 5 is a schematic block diagram specifically showing an example of an inspection apparatus A for inspecting foreign particles and the like, in accordance with the present invention.

The photoelectric transducer 106 can receive only scattering light generated by a foreign substance by shielding a diffracted light pattern generated by the repetition pattern of a memory cell or the like on the sample 1 to be inspected by the use of a spatial filter 105a shown in FIG. 5. Here, the CPU 110a may be connected to a server 115 storing the inspection data or a terminal 120 via a network 114. Further, in the inspection apparatus A, as shown in FIG. 5, it is required to previously input a plurality of inspection conditions Ta, Tb, Tc, ... from an input device 111a and to store them as a group of inspection data 300a. Still further, in the inspection apparatus A, as shown in FIG. 5, it is necessary to store in the storage device 113a a group 11a of inspection data, which is the results of inspection obtained from the CPU 110a under a plurality inspection conditions Ta, Tb, Tc, ....

Further, also in the inspection apparatus A for inspecting a foreign substance, it is possible to discriminate a foreign substance from a scratch (flaw) based on the difference between the foreign substance and the scratch by calculating the quantity of feature of the defect detected by the judgment circuit 109a.

Still further, in the inspection apparatus A for inspecting a foreign substance, it is also recommended that a polarizing laser be obliquely applied to the sample 1 to be inspected, and that scattering light, generated by the edge of a circuit pattern formed on the sample 1 to be inspected, be shielded by means of an analyzer, and that scattering light generated by a foreign substance be made to pass through the analyzer and be detected by the photoelectric transducer 106.

Figure 3:
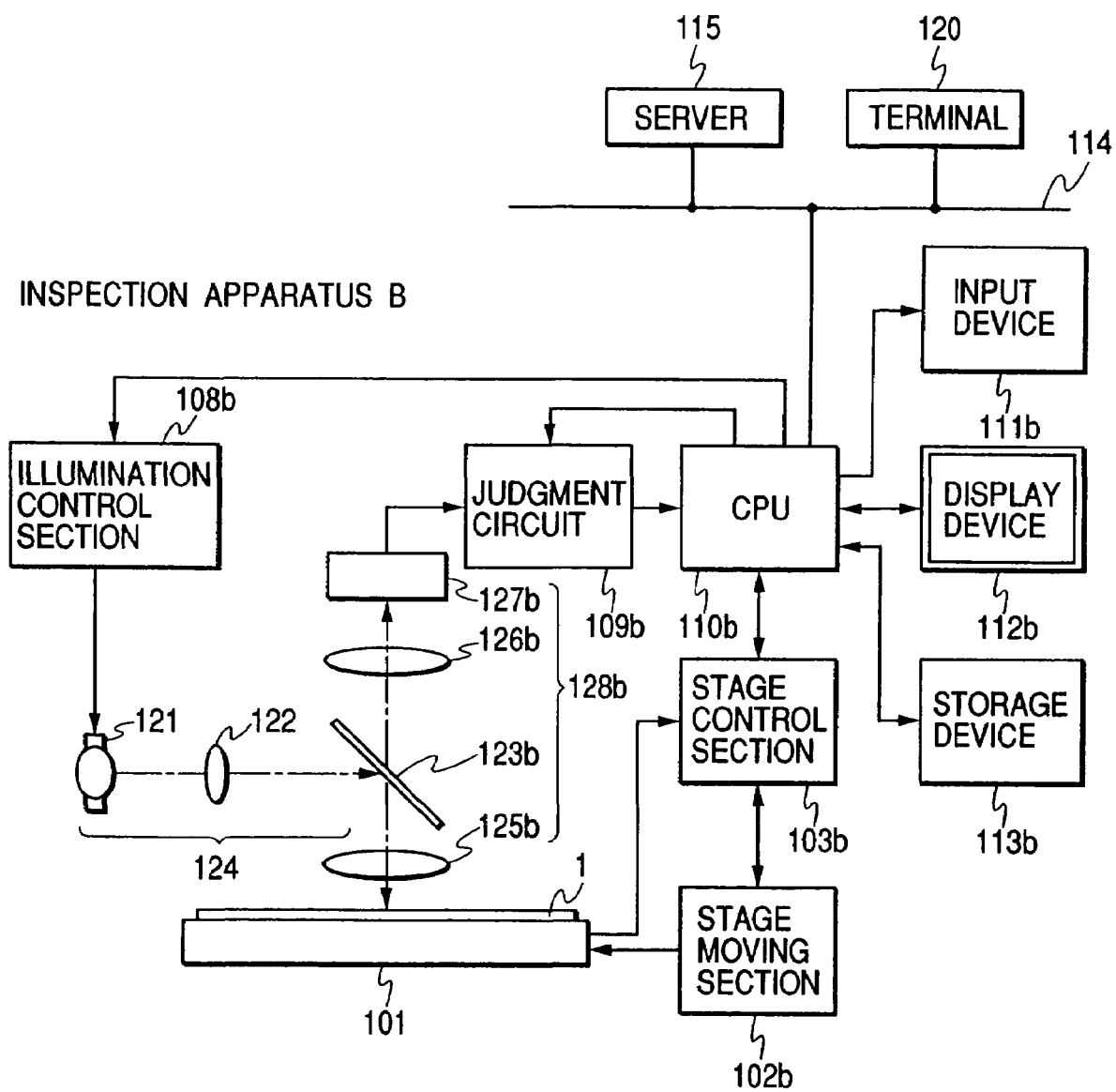
FIG. 3 is a schematic block diagram showing an example of an inspection apparatus B for inspecting defects of a circuit pattern and the like, in accordance with the present invention.

An inspection apparatus B shown in FIG. 3 is the one used for inspecting microscopic uneven defects and defects in a circuit pattern and provided with a vertical illuminating optical system 124, which is composed of a light source 121 for vertical illumination, a collective lens 122, and a mirror 123b such as a small mirror, a half mirror, a polarization beam splitter, and the like, and a detecting optical system 128b composed of an objective lens 125b, an image forming lens 126b, and a photoelectric transducer 127b.

In the case where the polarization beam splitter 123b is used, it is recommended that a light source to emit a polarizing laser beam be used as the light source 121, and that illumination light circularly polarized with a $\lambda/4$ plate interposed between a polarization beam splitter, which is the mirror 123b, and the objective lens 125b be applied to the sample 1 to be inspected, and that scattering light produced by the defects is transmitted through the polarization beam splitter which is the mirror 123b.

In any case, it is desirable also in the inspection apparatus B that the specular reflection light from the surface of the sample 1 to be inspected, caused by vertical illumination, is shielded, for example, by a spatial filter or the like, to prevent the photoelectric transducer 127b from receiving the specular reflection light, and that the photoelectric transducer 127b receives scattering light generated by the above-mentioned defects. That is, the configuration, other than the illuminating optical system 124, of the inspection apparatus is substantially constituted in the same way as the inspection apparatus A.

A judgment circuit 109b aligns an inspection image signal which is produced by the photoelectric transducer 127b, which receives an optical image of a circuit pattern formed by an image forming lens 126b, with a standard image signal (reference image signal) produced by a neighboring chip or cell, and compares the inspection image signal and the standard image signal, which are aligned with each other, to extract a differential image from both the image signals, and judges the extracted differential image by a previously set predetermined threshold to detect an image signal indicating a circuit pattern defect, and judges the circuit pattern defect based on the detected image signal indicating a foreign substance or, if necessary, further calculates the quantity of features (area, length, center of gravity, and the like) of the detected image signal indicating the circuit pattern defect and judges the circuit pattern defect based on the calculated quantity of features.

Figure 4:
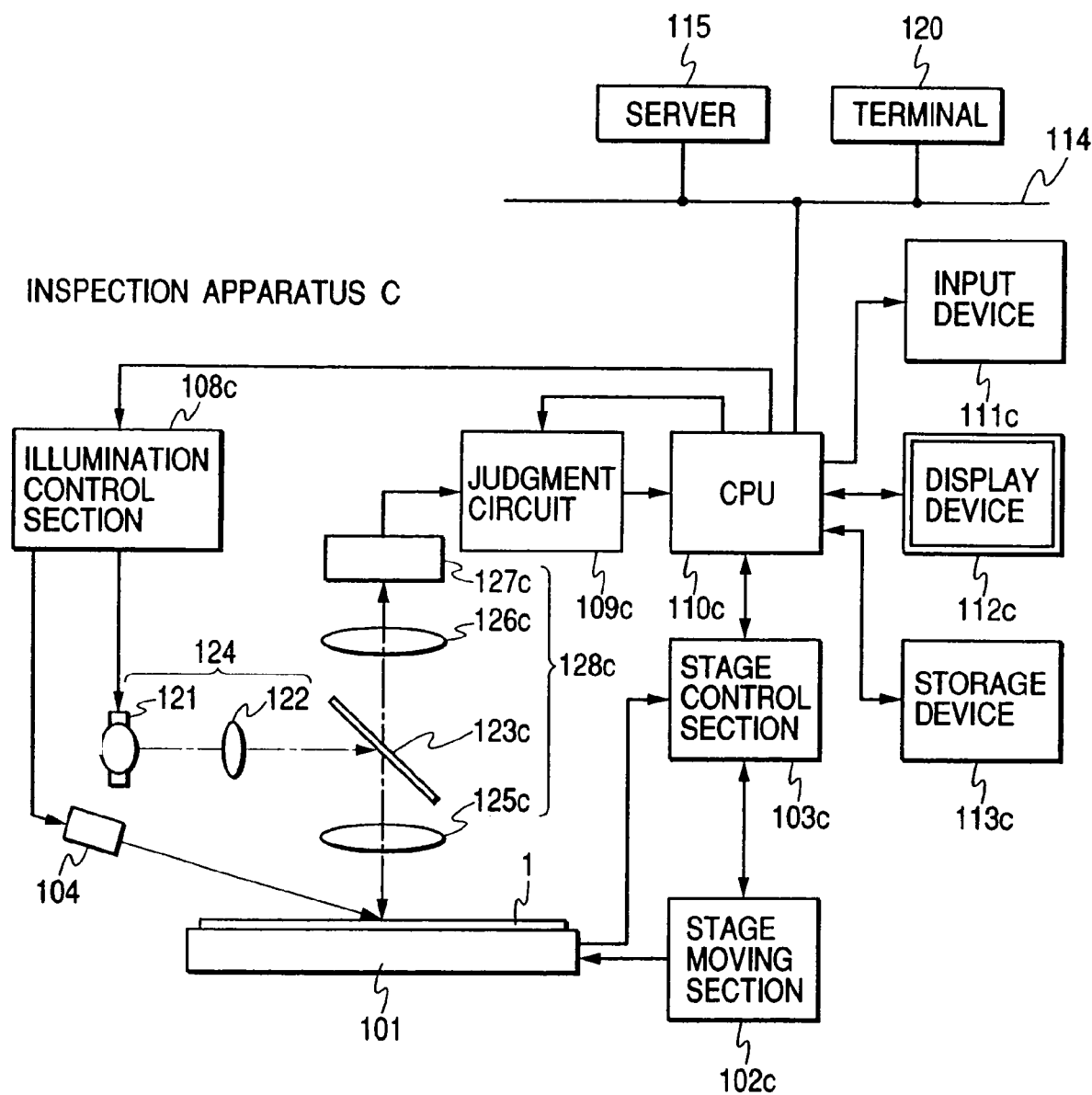
FIG. 4 is a schematic block diagram showing an example of an inspection apparatus C for inspecting defects of a circuit pattern and the like, in accordance with the present invention.

Also, an inspection apparatus C, as shown in FIG. 4, is provided with both of the obliquely illustrating optical system 104 shown in the inspection apparatus A in FIG. 2 and the vertical illuminating optical system 124 shown in the inspection apparatus B in FIG. 3, and a detecting optical system 128c having approximately the same configuration as, for example, the detecting optical system 128b shown in FIG. 3. In this manner, since the inspection apparatus C is provided with both of the illuminating optical systems, if the respective optical systems are alternately applied light to the sample 101 to be inspected, respectively, then the photoelectric transducer 127c receives different optical images formed by the respective illuminations, which makes it possible to discriminate between a foreign substance and a circuit defect and hence to inspect them with high sensitivity. Naturally, it is necessary to change an inspection algorithm in the judgment circuit 109c between the judgment of the foreign substance and the judgment of the circuit pattern defect. Also, this configuration makes it possible to discriminate the foreign substance and the circuit pattern defect from scratches of microscopic dips in the inspection by comparing the intensity signals of the scattering light obtained from the photoelectric transducer 127c by the respective optical systems and by calculating a ratio of the intensity signals.

In addition to this, as still another inspection apparatus, there is provided an appearance inspection apparatus using a SEM (Secondary Electron Microscope).

Here, in the inspection apparatus A, as shown in FIG. 5, it is necessary to previously input a plurality of inspection conditions Ta, Tb, Tc, by the use of an input device 111a and to store them in a storage device 113a as a group 200a of inspection conditions. Also, a group 300a of inspection data under the plurality of inspection conditions Ta, Tb, Tc, . . . , which is obtained from a CPU 110a is stored in the memory device 113a.

Here, also in the inspection apparatus B or C, as is the case with the inspection apparatus A shown in FIG. 5, it is necessary to previously input a plurality of inspection conditions Ta, Tb, Tc, . . . by the use of an input device 111b or 111c and to store them in a storage device 113b or 113c as a group 200b or 200c of inspection conditions. Also, in the inspection apparatus B or C, as is the case with the inspection apparatus A shown in FIG. 5, a group 300a of inspection data under the plurality of inspection conditions Ta, Tb, Tc, . . . , which is obtained from a CPU 110b or 110c, is stored in a memory device 113b or 113c.

Next, a group 10 of plural kinds of inspections with respect to the sample 1 to be inspected will be described in detail.

The plural kinds of inspections mean the plural kinds of inspections due to a difference in optical conditions such as:

(a) in the inspection using the same inspection apparatus A, B, or C, (a-1) illuminating conditions (for example, in the case of illuminating optical systems 104, 124 shown in FIG. 2, FIG. 3 and FIG. 4, among the illuminating conditions is the quantity of illuminating light controlled by an illumination control section 108a, 108b, or 108c; in the case where a light source is a laser light source, a laser power emitted from the laser light source controlled by the illumination control section 108a, 108b, or 108c is one of the illuminating conditions; also, if the angle of the oblique illumination can be changed by the illumination control section 108b or 108c in the illuminating optical system 104 shown in FIG. 2 or FIG. 4, then the angle of the oblique illumination is included in the illuminating conditions; and, in the case where the inspection apparatus is provided with a plurality of illuminating optical systems, the switching control of the plurality of illuminating optical systems is included in the illuminating conditions); and detecting conditions (for example, focus controlling conditions—focus offset and the like), controlling conditions of the phase and pitch of a light shielding pattern in the case of a variable spatial filter disclosed in Japanese Unexamined Patent Publication No. 6-258239, the moving speed of a stage 101 controlled by the stage control section 103); and (a-2) plural kinds of inspections due to a difference in an inspection algorithm (for example, a difference in a judgment parameter such as a threshold map (threshold image) to judge a foreign substance and a defect, and a difference in an alignment accuracy between a detected image signal and a standard image signal.

In this connection, in the case where the sample 1 to be inspected is a semiconductor wafer, the detection signal detected by the photoelectric transducer 106, 107b, or 107c has variations due to a subtle difference in the process which does not cause a defect, noises during the detection, and the like. That is, signal levels from corresponding pixels between chips formed on the semiconductor wafer are not the same values but have variations. To be more specific, the detection signals are different in variations among regions having different structures in the circuit pattern (for example, in the case of a memory LSI, a memory cell region, a peripheral circuit region, and the other region).

As a result, in the regions where variations in the detection signal are small can be detected a defect causing a small change in the detection signal such as a foreign substance and the like, whereas in the regions where the variations in the detection signal are large can be detected only a defect causing a large change in the detection signal. Accordingly, a threshold which is one of the inspection conditions corresponds to a value obtained by multiplying a variation (standard deviation σ) in the detection signal among the corresponding regions among the chips by a magnification m. That is, this threshold level corresponds to the condition of the underlying layer (repetition pattern region, region with an extremely rough surface, region with a thick film, region with a small size pattern, or the like).

Therefore, in the case where a map of various thresholds is prepared as one of the plurality of inspection conditions, if the threshold is low, small defects can be detected, but false information increases, and if the threshold is high, only large defects can be detected. As a result, also in the threshold map, there is an optimal condition for the underlying condition.

Also, in the case where the quantity of light (laser power) is changed as one of the plurality of inspection conditions, if the laser power is increased, sensitivity is also increased to enable the detection of a small defect like a small foreign substance but scattering light from the underlying layer is also increased to increase the area of the saturated regions (regions not to be inspected), and if the laser power is decreased, the sensitivity is also decreased and hence only large defects can be detected but scattering light from the underlying layer is decreased to extremely decrease the area of the region not to be inspected. Therefore, there is an optimal condition also for the laser power according to the size of a foreign substance to be detected and the like and the condition of the underlying layer.

Also, the phase and pitch of the light shielding potion of the spatial filter are required to meet the structure of the underlying layer of the sample to be inspected.

The plural kinds of inspections fundamentally mean (b) an error (variation) due to the difference between inspection apparatuses in the inspection using a plurality of inspection apparatuses of the same kind or approximately the same kind.

The plural kinds of inspections mean (c) in the inspection using inspection apparatuses of different kinds, (c-1) plural kinds of inspections due to a difference in optical conditions such as illuminating conditions (for example, method of applying an illuminating beam to the sample 1 to be inspected based on a difference in the light source such as laser, white light, electron beam, ion beam, x-ray, or the like, wavelength of illuminating light, direction of illumination, angle of illumination, and a combination of a plurality of illuminations) and detecting conditions (for example, a difference in the kind of detector such as a CCD sensor, a TDI sensor, an X-ray detector, a secondary electron detector, a photomultiplier, a secondary ion detector, and a difference in detecting optical system), and (c-2) the plural kinds of inspections due to a difference in an image processing algorithm with respect to the image signal obtained from various kinds of optical conditions.

Next, (a) a first preferred embodiment in accordance with the present invention for setting an optimal inspection condition will be described using FIG. 6 to FIG. 8 in which a plurality of inspections is performed as a single unit under a plurality of different inspection conditions by the use of the same inspection apparatus. FIG. 6 and FIG. 8 show the cases where the inspection apparatus A shown in FIG. 2 can inspect foreign particles and scratches (defects), and FIG. 7 show the case where the inspection apparatus A can inspect only foreign particles.

The inspection conditions, as described above, include the ones related to adjustable, controllable factors of the illuminating optical system such as quantity of illumination, polarization of illuminating light, and direction of illumination; the ones related to the adjustable, controllable factors of the detecting optical such as the phase and pitch of light shielding pattern of the spatial filter, and parameters to be changed in setting (for example, threshold map) of the inspection algorithm, and these inspection conditions can be set and stored in the storage device 113a by the use of the input device 111a. Naturally, the CPU 11a has a function to control the whole inspection apparatus and controls the illumination control section 108a, the stage control section 103a, the judgment circuit 109a, and the spatial filter 105a such that the sample 1 to be inspection can be inspected based on the set inspection conditions Ta, Tb, Tc, . . . .

Figure 7:
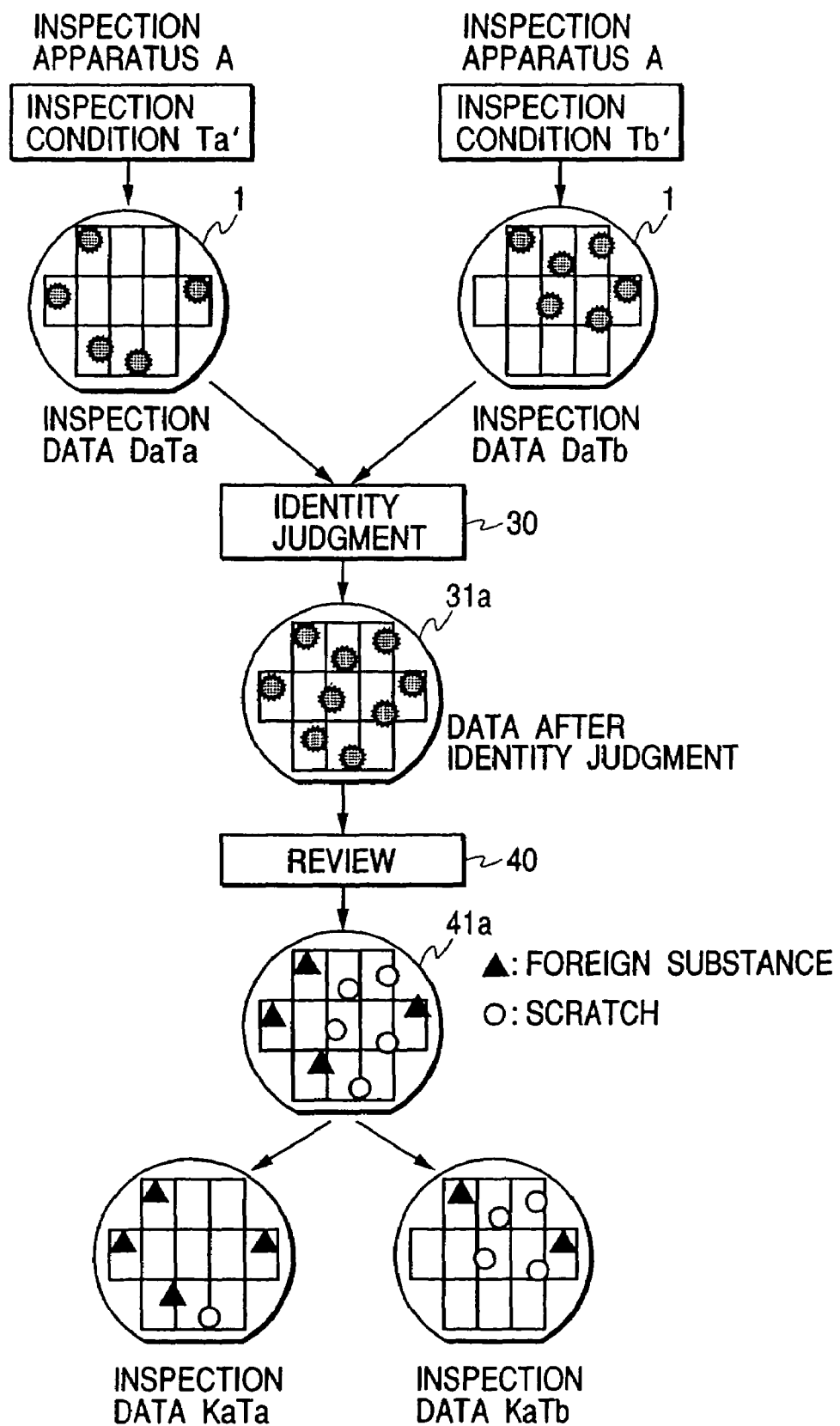
FIG. 7 is an illustration to show a second example of a processing flow for selecting an optimal inspection condition to a sample to be inspected, in accordance with the present invention.
Figure 8:
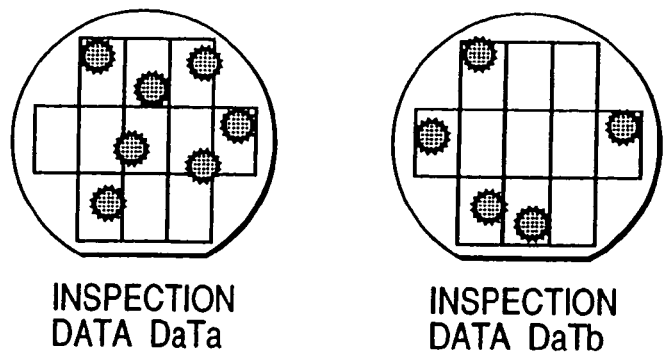
FIG. 8 is an illustration to show inspection data obtained by inspecting a sample to be inspected under a plurality of inspection conditions.
Figure 9A:
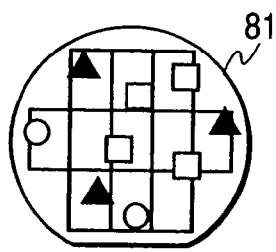
FIG. 9 is an illustration to show examples of various kinds of data arbitrarily selected from check data for display in order to facilitate reviewing or analyzing results of inspection.
Figure 9B:
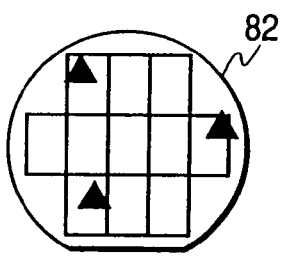
Figure 9C:
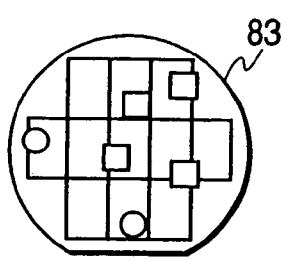
Figure 9D:
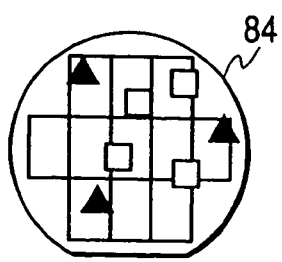
Figure 9E:
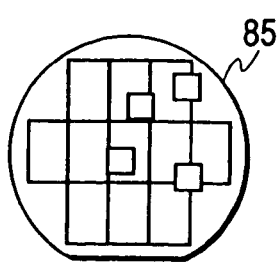

First, in the case of the inspection apparatus A capable of inspecting a foreign substance and the like with excellent sensitivity, as shown in FIG. 2 and FIG. 5, when the same sample 1 to be inspected, which is manufactured in the manufacturing process to be inspected, is inspected as a single unit with the inspection apparatus A under a plurality of inspection conditions Ta, Tb, Tc, . . . stored in the storage device 113a, as shown in FIG. 6 to FIG. 8, a group 111a of inspection data DaTa, DaTb, DaTc, . . . , which are the results of the inspections under the respective inspection conditions, can be obtained, with respect to coordinates set for the sample 1 to be inspected and are stored in the storage device 113 by the judgment circuit 109 and the CPU 110a.

As the inspection data, not only the coordinates of detected particles but also the quantity of features of the respective detected particles or the brightness image signals of the detected particles, which are obtained from the judgment circuit 109, are stored as corresponding pairs so that they can be reviewed or analyzed and classified. Here, the error between the stage coordinates obtained by the stage control section 103 and the coordinates set on the sample 1 to be inspected can be corrected in the CPU 110a by detecting the reference mark formed on the sample 1 to be inspected.

Next, the CPU 110a compares the coordinates of the detected particles of a plurality of inspection data obtained under the respective inspection conditions to judge the identity of the positions of the detected particles and checks the plurality of inspection data based on the identity judgment and stores the data 31a of the results of check (data after the identity judgment) in an internal memory (not shown) or the storage device 113.

In this connection, in the case of the present preferred embodiment, only the inspection conditions are changed and hence, basically, it is essential for the judgment of identity only that alignment errors based on the stage control of the sample 1 to be inspected and detection errors caused according to size of the detected substance and the intensity of the signal detected from the detected substance are taken into account. Therefore, when the spacing between the detected particles detected under the respective inspection conditions is smaller than two times the above-mentioned alignment error, it is recommended that the detected particles be judged to be the same substance.

That is, when detection regions are set two-dimensionally according to the alignment error around the positions of the detected particles detected under the respective inspection conditions and the set detection regions overlap each other, the detected particles may be judged to be the same substance. As described above, by performing an identity judgment on the plurality of inspection data inspected and obtained as a single unit under the plurality of inspection conditions, the number of detected particles to be analyzed can be decreased, which is described below, and by outputting the data after the identity judgment, the distribution of the detected particles can be recognized instantaneously.

Next, the CPU 110a displays the data 31a of check results stored in the storage device 113 and the quantity of feature or the brightness image signal of the detected substance on the display device 112 in the analysis processing section (step) 40. A category (foreign substance, false information, scratch (flaw)) including a size is assigned by the input device 111 to each detected substance, based on the quantity of feature and the brightness image signal of the detected substance, which are displayed on the display device 112, to thereby produce the classified review result (analysis data) 41a of the detected substance. The classified review result 41a and coordinates of the detected substance are stored in the internal memory or the storage device 113. Here, the size of the detected substance can be assigned by determining the area of the image signal indicating the detected substance. Also, the CPU 110a may automatically classify each detected substance by the quantity of feature thereof by means of ADC (automatic defect classification) and may automatically assign a category to the detected substance. This ADC is provided as an additional function of the inspection apparatus or as a dedicated automatic review device.

In this connection, as a method of displaying the data 31a of check results, when the inspection data DaTa, DaTb under the inspection conditions shown in FIG. 8 are obtained, various methods shown in FIG. 9 and FIG. 10 are proposed so as to facilitate reviewing or analyzing the data. That is, FIG. 9(a) shows the logical OR data 81 of both of the inspection data DaTa, DaTb, FIG. 9(b) shows the identity data 82 of both of the inspection data DaTa, DaTb, FIG. 9(c) shows the non-identity data 83 of both of the inspection data DaTa, DaTb, FIG. 9(d) shows the data 84 of both of the inspection data DaTa, and FIG. 9(d) shows the data 85 only under the inspection condition Tb.

In FIG. 10(a), the inspection data are displayed with their inspection conditions distinguished from each other, and in FIG. 10(b), there are displayed the number of detections of the detected particles when the inspections are performed on them under different inspection conditions. By selecting various types of displays for the data 31a of check results, the data 31 of check results can be checked against the inspection conditions, whereby the detected particles can be easily classified into the above-mentioned categories.

The selection of the various types of displays includes: (1) selection of the logic OR data 81; (2) as for the identity data 82, selection of the data having a low possibility of being false information, or selection of the non-identity data 83 as the detected substance which resists appearing even if the inspection conditions are changed; (3) selection of the data obtained by adding the identity data 82 to the non-identity data 83 in (2) at an arbitrary ratio, (4) selection of the data of the number of detections smaller than an arbitrary number of detections out of the data of the number of detections of the detected particles under the plurality of inspection conditions; (5) selection of data obtained by specifying the region on the sample to be inspected with respect to the respective data in the above-mentioned (1) to (4); (6) selection of the data extracted at an arbitrary ratio from the respective data in the above-mentioned (1) to (4); and (7) selection of a combination of the above-mentioned (5) and (6).

By selecting these various types of displays and displaying them on the display device 112, the state where the detected particles are detected from the surface of the sample to be inspected can be grasped to facilitate analyzing the detected particles, that is, classifying them into the categories. For example, as for the false information, there is little possibility that it is detected as identity data and hence the selection of the data in (2) may be meaningful. Also, since the false information is small in the number of detections and the substance newly detected under a given inspection condition (whose category is determined in some case by the given inspection condition) is small in the number of detections, the selection of the data in (4) is meaningful. Further, as described above, since the detection of the defects is largely affected by the underlying region of the sample to be inspected (including a peripheral region, a central region, and a region in a chip), the selection of the data in (5) is meaningful. Still further, when the inspection conditions do not become suitable, many detected particles are produced on the sample to be inspected. Hence, if they are checked against each other and the checking results are outputted on the display at a time, then the analysis of the checking results is very difficult. Therefore, in order to display a part of the defected particles, the selection of the data in (6) is necessary.

Next, the CPU 110a feeds back the analysis data (review results) 41a with categories assigned thereto to the group of inspection data 11a to form a group 51a of inspection data KaTa, KaTb, KaTc, . . . , which are classified by the inspection conditions, for example, in an analysis data compiling section (step) 50 and stores them in the storage device 113. Then, the CPU 110a displays the stored group of inspection data 51a, for example, to the display device 112 to inform an operator that an inspection condition Tb is an optimal inspection condition under which false information is little included and foreign particles and the like can be detected, which results in enabling the operator to select and set the optimal inspection condition Tb with respect to the sample 1 to be inspected to the above-mentioned inspection apparatus A by the use of the input device 111. Therefore, after the optimal inspection condition is selected and set to the inspection apparatus A, the inspection apparatus A can inspect the sample 1 to be inspected, manufactured in a given manufacturing process, under the inspection condition most suitable to the surface condition of the sample 1 to be inspected.

Figure 12:
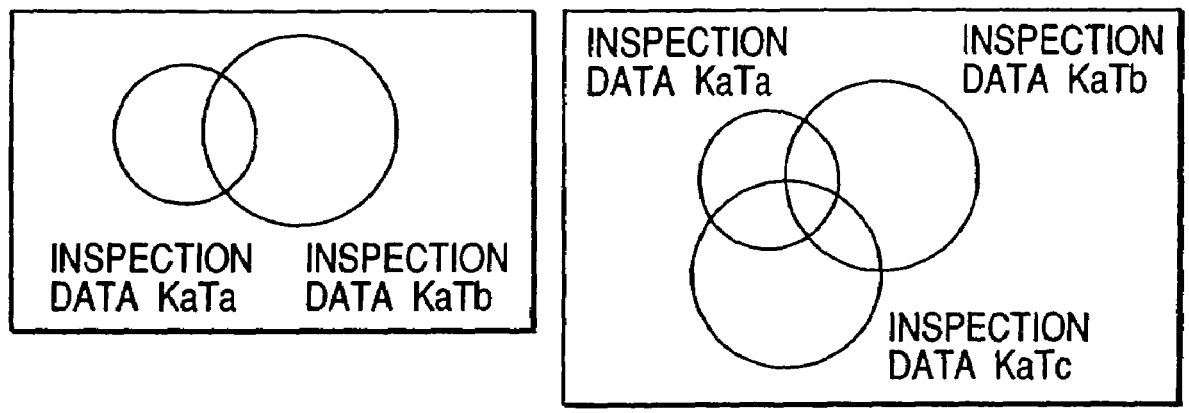
FIG. 12 is an illustration to show the state of checking the inspection data obtained under various inspection conditions against each other.
Figure 13:
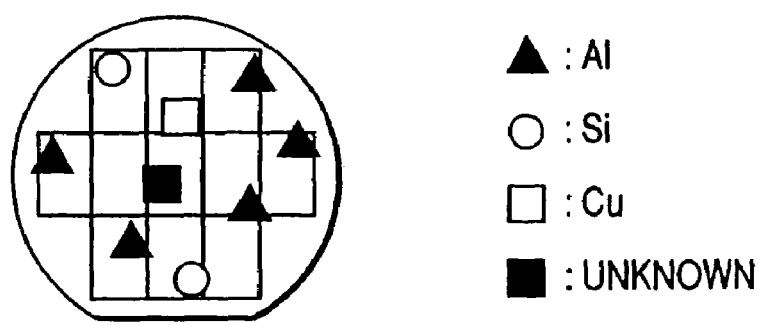

In this connection, various types of displays such as map, list, or the like are thought as the methods of displaying the group of inspection data 51a including the plurality of inspection data Ka on the display device 112. In FIG. 11, there is shown the form of list in which inspection conditions are described. As is clear from this form of list, the inspection conditions B and C have little false information and hence can be selected as optimal inspection conditions on the screen of the display device 112 by the use of the input device 111. Also, since threshold images/histograms are displayed on the screen, it is possible to judge whether the threshold is proper or not. Also, the inspection data can be displayed by means of Venn map shown in FIG. 12. Also, the inspection data K of the respective inspection conditions can be discriminated by a character, a symbol, a numeral, a figure, a color or a size, as shown in FIG. 10, as is the case with the display of the data 31a of check results.

Further, by analyzing the sample to be inspected, which is reviewed and classified, by means of a mass spectrometer or an X-ray spectrometer, the material of the foreign substance is analyzed into Al, Si, Cu, and unknown. Then, by inputting this data into the CPU 110(20), the material of the foreign substance can be displayed on the display device 112 and the category of the foreign substance can be determined with reliability and the cause of generation of the foreign substance can be tracked down.

As described above, according to the above-mentioned preferred embodiments, if a sample 1 to be inspected, manufactured by a given manufacturing process, is inspected in a single unit under a plurality of inspection conditions with an inspection apparatus and detected particles are checked against each other, the detected particles can be reviewed and classified at a time. As a result, time required to determine an optimal inspection condition can be largely shortened.

Next, (b) an inspection of a preferred embodiment in accordance with the present invention in the case where the inspection is performed on a sample to be inspected with a plurality of inspection apparatuses of the same kind or approximately the same kind will be described with reference to FIG. 14.

In the present preferred embodiment, the CPU 20 constituting an identity judgment processing section (step) 30, an analysis processing section (step) 40, and an analysis data compiling section (step) 50 may be connected to each of a plurality of inspection apparatuses through a network, or may be composed of a CPU 110 which is built in each of the plurality of inspection apparatuses. In the latter case, however, the CPUs 110 built in the plurality of inspection apparatuses are connected to each other through a network. Also, to the above-mentioned CPU 20 are connected an input device 111, a display device 112, and a storage device 113.

Figure 14:
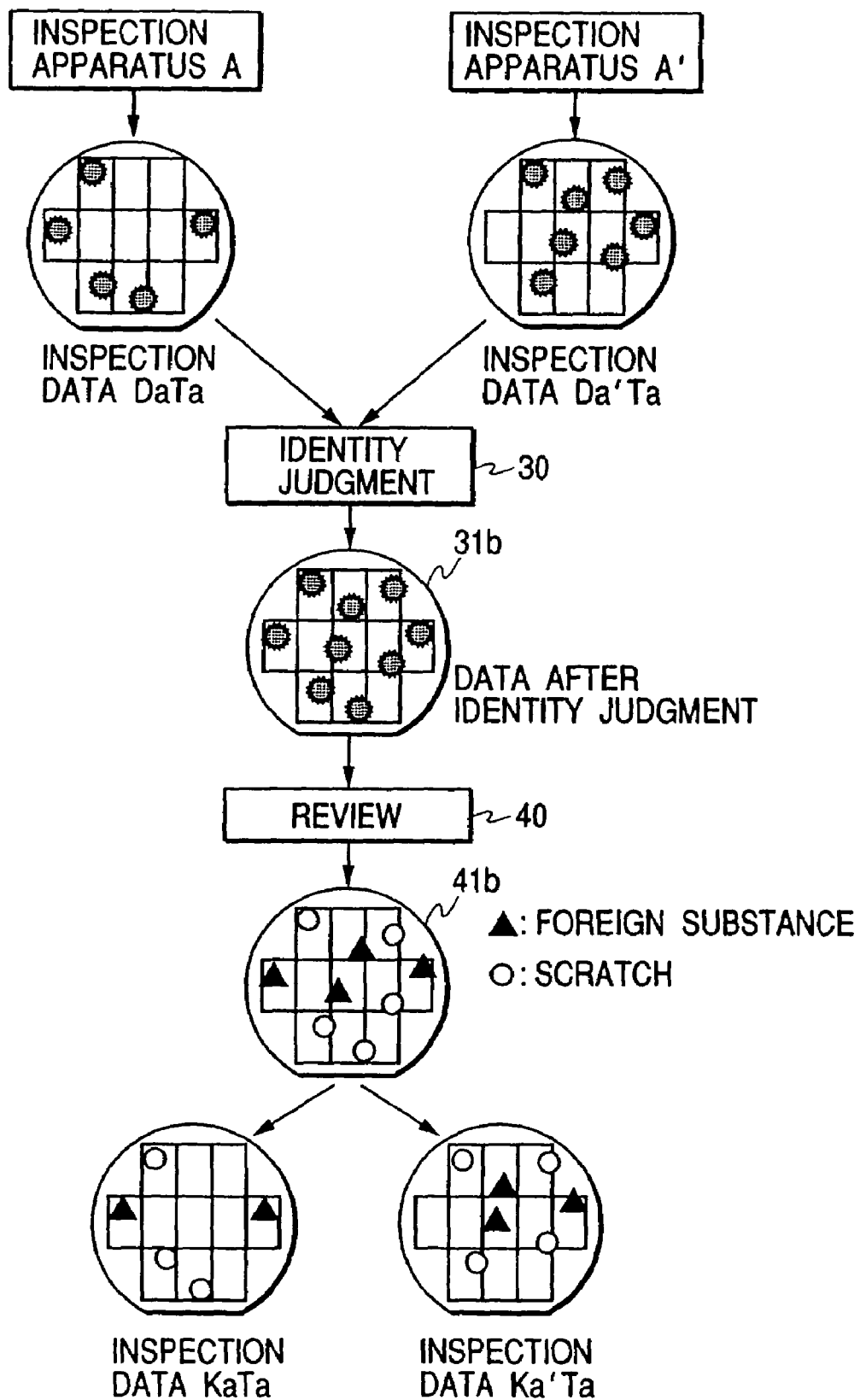
FIG. 14 is an illustration to show an embodiment of a processing flow for selecting an optimal inspection apparatus out of a plurality of inspection apparatuses of the same kind or approximately the same kind to a sample to be inspected, in accordance with the present invention.

In the case of this preferred embodiment, as shown in FIG. 14, the same sample 1 to be inspected, manufactured in given manufacturing process, is inspected by the inspection apparatus A and the inspection apparatus A', both of which are of the same kind or approximately the same kind, under the same inspection condition Ta and inspection data DaTa, Da'Ta can be obtained. The CPU 20 (110) performs an identity judgment on the detected substance in the state where error components caused by the apparatus difference between the inspection apparatus A and the inspection apparatus A'are added to the inspection data DaTa, Da'Ta to produce the data 31b of check results. The above-mentioned error components include, for example, an error caused by the accuracy of the transfer mechanism of the stage 101 and the like, a detection error caused by, for example, a rotary encoder or a linear encoder for detecting the displacement of the stage 101, a conversion error in the case where coordinates are different between the respective inspection data, an assembly error of the inspection apparatus itself, and a positioning error caused by a misalignment caused when the sample 1 to be inspected is mounted on the respective inspection apparatuses A, A'.

The subsequent procedures of processing the inspection data are the same as those of the preferred embodiment shown in FIG. 5, FIG. 6, and FIG. 7. Here, review results (analysis data) 41b are the review results based on the data 31b of check results. In this manner, further detailed investigation based on the group of inspection data 51b obtained for the respective inspection apparatuses enables an apparatus analysis of the inspection apparatuses of the same kind or approximately the same kind.

As a result, it is possible to select the inspection apparatuses A, A'suitable for the sample 1 to be inspected, manufactured in a given manufacturing process, from the inspection data KaTa, Ka'Ta (51b) obtained for the respective inspection apparatuses. In the case of the preferred embodiment shown in FIG. 14, since the inspection apparatus A' can comparatively well detect foreign particles and scratches, the inspection apparatus A' comes to be selected. Here, at this time, by changing the inspection conditions in the same way for the respective inspection apparatuses A, A', the inspection accuracy can be improved to a suitable extent.

Figure 15:
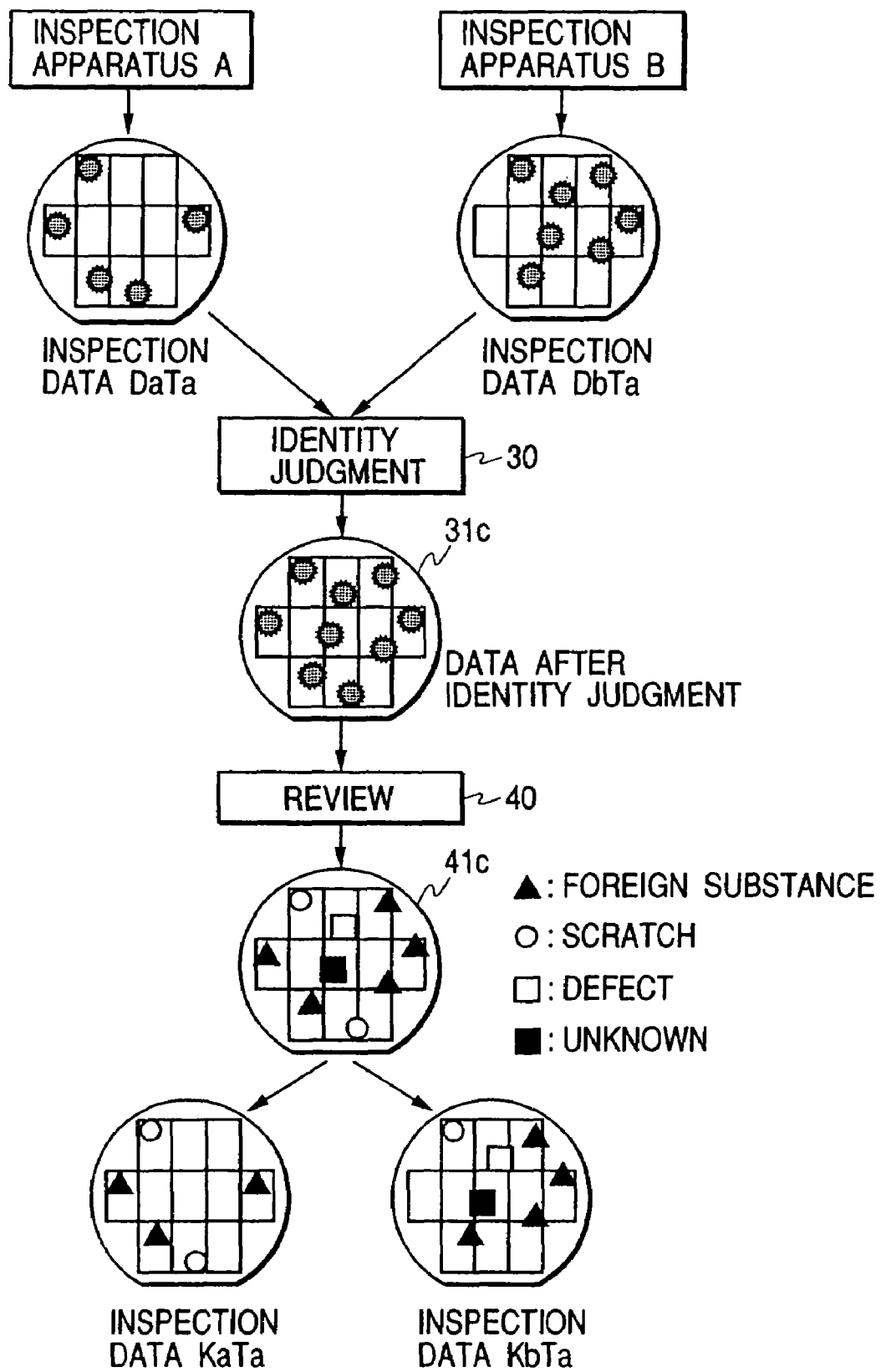
FIG. 15 is an illustration to show an embodiment of a processing flow for selecting an optimal inspection apparatus among a plurality of inspection apparatuses of different kinds to a sample to be inspected, in accordance with the present invention.

Next, (c) an inspection in accordance with the present invention in the preferred embodiment in which the inspection is performed with inspection apparatuses of different kinds will be described with reference to FIG. 15. Also in this preferred embodiment, the CPU 20 is composed in the same manner as the preferred embodiment in (b). As shown in FIG. 15, the sample 1 to be inspected, manufactured in a given manufacturing process, are inspected by an inspection apparatus A and an inspection apparatus B, which are different in kind from each other, under the same inspection condition Ta, and inspection data DaTa, DbTa can be obtained. A CPU 20 (110) makes an identity judgment on a detected substance in the state where an error component caused by the apparatus difference between the inspection apparatus A and the inspection apparatus B, which are different in kind from each other, is added to the inspection data DaTa, DbTa in an identity judgment processing (step) 30 to thereby produce the data 31c of check results.

In the case of this preferred embodiment, the error component is set for each kind of the inspection apparatus. That is, the CPUs 110 of the respective inspection apparatuses A, B obtain inspection data indicating abnormalities such as a foreign substance, a defect, and the like from a judgment circuit 109 and determine coordinate data indicating the position information of the detection data based on a stage coordinate system given by a stage control section 103 and store them in a storage device 113. Therefore, for example, the identity judgment processing section 30 of the CPU 20 makes one arbitrary coordinate data among coordinate data indicating position information of the detected particles of the inspection data obtained from the CPUs 110 of two or more arbitrary inspection apparatuses, out of the group of inspection data 11 obtained from the CPUs 110 of the respective inspection apparatuses and shown in FIG. 1, standard coordinate data, and compares the standard coordinate data and the remaining other coordinate data to make an identity judgment on the detected particles. Here, the identity judgment processing section 30 makes the identity judgment on the detected particles based on the above-mentioned apparatus error components $Z_1$, $Z_2$ of the respective inspection apparatuses.

Figure 16:
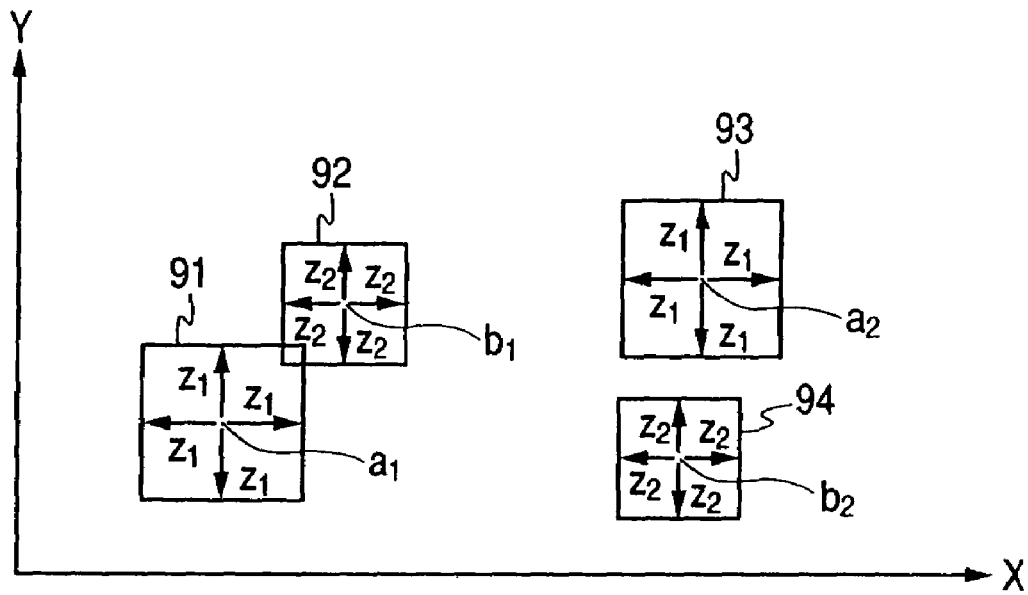
FIG. 16 is an illustration to show a first embodiment in which an identity judgment is performed on a detected substance based on an error component due to a difference between inspection apparatuses.
Figure 17:
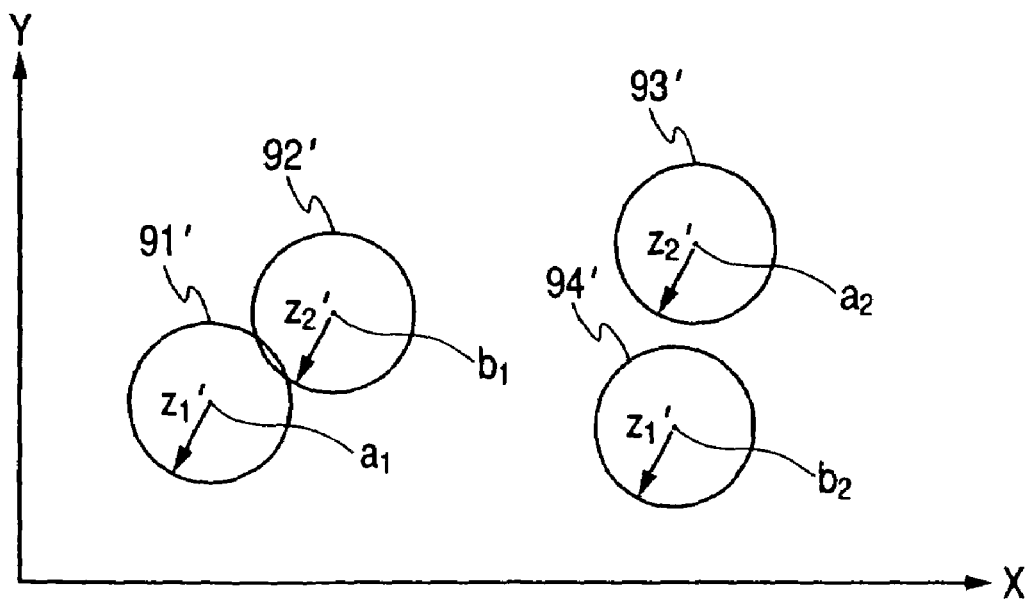
FIG. 17 is an illustration to show a second embodiment in which an identity judgment is performed on a detected substance based on an error component due to a difference between inspection apparatuses.
Figure 18:
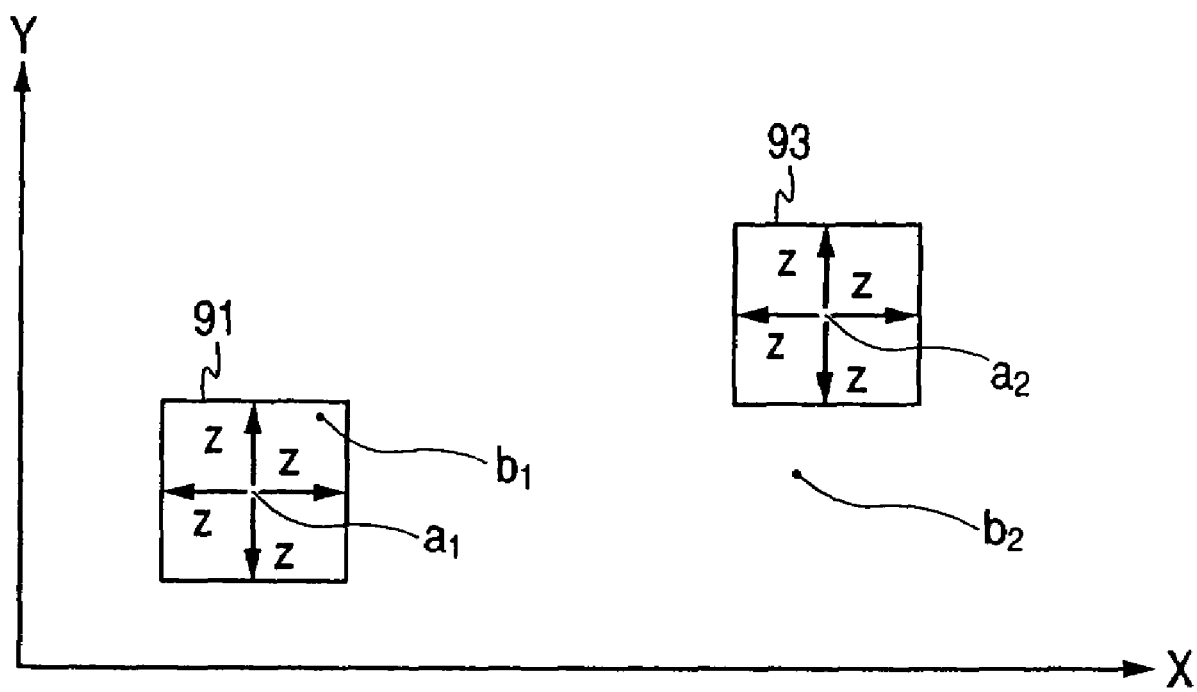
FIG. 18 is an illustration to show a third embodiment in which an identity judgment is performed on a detected substance based on an error component due to a difference between inspection apparatuses.

Here, it is thought that the accuracy of coordinates of the inspection data used for the identity judgment are largely different from each other because of the size of the detected substance, the intensity of signal of the detected substance, and the kind of the inspection apparatus. Also, as the methods for making the identity judgment, there are various methods as shown in FIG. 16 to FIG. 18. Each of them shows in one coordinate system the respective coordinate data indicating coordinates of the substance detected by the inspection apparatus A and the inspection apparatus B. Reference characters a1, a2 designate the particles detected by the inspection apparatus A and reference characters b1, b2 designate the particles detected by the inspection apparatus B. Reference characters 91, 92 designate the regions of the detected particles a1, b1. Reference characters 93, 94 designate the regions of the detected particles a2, b2. Each of the detection regions 91, 92 is constituted by a square whose center is the point having coordinates of the detected substance a1 or b1 and whose side is two times the detection error component $Z_1$ of the inspection apparatus A itself. Each of the detection regions 93, 94 is constituted by a square whose center is the point having coordinates of the detected substance a2 or b2 and whose side is two times the detection error component $Z_2$ of the inspection apparatus B itself. Identity judgment of the detected particles is made according to whether the detection regions of the respective detected particles overlap each other. Since the detection regions 91, 92 of the detected particles a1, b1 overlap each other, the detected particles a1, b1 are judged to be identical. Since the detection regions of the detected particles a1 and b2, a2 and b1, and a2 and b2 do not overlap each other, the respective detected particles a1 and b2, a2 and b1, and a2 and b2 are judged not to be identical. The use of this method enables more unerring identity judgment.

In addition to the above method, there are proposed, for example, a method in which each of the detection regions, as shown in FIG. 17, is composed of a circle having a center at the point having coordinates of each detected substance and a radius of the detection error $Z_1$ or $Z_2$, a method in which the detection region is applied to one detection data, as shown in FIG. 18, or a combination of these methods.

As described above, by displaying the data 31c of the checking results obtained from the identity judgment on the display device 112, it is possible to instantaneously recognize how the particles detected by the inspection apparatuses A, B are distributed. Also, when a detailed analysis is made, it is possible to analyze the inspection data DaTa, DbTa produced by the inspection apparatuses A, B as a single unit, instead of analyzing them separately.

When the inspection apparatuses are different from each other, it is thought that the kinds and the number of items of the data stored with respect to the detected particles such as the form of file, the method of determining coordinate axes, the accuracy of coordinates, and the like may be different in the group 11 of inspection data between the inspection apparatuses. In view of these, it is desirable that the data 31c after the identity judgment, which are the results of checking, can respond to all the kinds and the number of items of the data that can be thought as the group 11 of inspection data. In the identity judgment processing section 30, the data 31c after the identity judgment needs to store the results of the identity judgment with respect to at least the group 11 of inspection data, and desirably further has the following conditions: the data 31c after the identity judgment are in the form of file that can be used by the analysis processing section 40, or can be converted into the form of file to be used by the analysis processing section 40, and can be fed back to the original group 11 of inspection data. At this time, the display examples shown as those of the data after the identity judgment need to be arbitrarily selected and be converted into files.

Next, a method of arbitrarily selecting objects to be inspected when the analysis processing section 40 reviews or analyzes them and makes a detailed inspection, such as classification, on them and an apparatus thereof will be described.

The data processing method used by the analysis processing section includes: a method of writing the respective data, shown in the display example of the data 31c after the identity judgment, to a file for use; a method of selecting the respective data out of the respective data at random in the arbitrarily determined proportions; a method of specifying the above-mentioned detection region on the display screen or by the coordinate and selecting the data in the detection region; a method of directly selecting the data displayed in the form of a map or a list; and a combination of these selecting methods.

Next, the method of reviewing, analyzing, and classifying the data will be described in detail.

That is, the analysis processing section 40 reviews or analyzes components of the inspection data selected in the above manner to make a detailed inspection such as classification on the inspection data. Reviewing or analyzing the date is performed manually or automatically and the results of classification are displayed and stored manually or automatically. The results of classification analyzed by the analysis processing section 40 are stored as a group 41c of analysis data.

An analysis data compiling section 50 performs an analysis data compiling on two or more arbitrary data among the group 41c of analysis data. This section 50 adds the results of classification of the defects, such as categories, to the data 31c after the identity judgment or a part of them.

The inspection data 51c compiled by the analysis data compiling section 50 are the summary of the above-mentioned inspection results of the sample 1 to be inspected.

Desirably, the data of the above-mentioned inspection, the identity judgment, and the analysis are stored as the inspection data 51*c*. Further, the analysis data compiling section 50 feeds back the inspection data 51*c* to the original group 11 of inspection data to provide the inspection data of each inspection apparatus in which the classification data are assigned to the sample to be inspected.

In the manner described above, it is possible to analyze the difference between plural kinds of inspection apparatuses with respect to a sample to be inspected, and further to perform plural kinds of inspections and analyses with efficiency in a short time, as is the case with the above-mentioned preferred embodiments (a), (b).

According to the preferred embodiments described above, the present invention can produce an effect of manufacturing a semiconductor device of high quality through a large number of manufacturing processes.

Also, according to the preferred embodiments described above, the present invention can produce an effect of inspecting particles to be detected such as foreign particles under an optimal inspection condition in accordance with the surface condition of a sample to be inspected, manufactured in various manufacturing processes.

Further, according to the preferred embodiments described above, the present invention can produce an effect of selecting a proper inspection apparatus for a sample to be inspected, manufactured in various manufacturing processes.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of inspecting a sample, comprising the steps of:
   inspecting a sample under a plurality of inspection conditions and obtaining inspection data with its position information on the sample;
   storing the inspection data with its position information on the sample which is obtained by inspecting the sample under each of the plurality of inspection conditions;
   checking identity of the stored inspection data obtained under each of the plurality of inspection conditions by the use of the stored position information on the sample;
   determining a position to be reviewed in detail from the identity checked inspection data;
   determining an inspection condition of the sample by the use of information obtained from an image of the position on the sample determined to be reviewed; and
   inspecting other samples under the determined inspection condition.

2. The method of inspecting a sample as set forth in claim 1, wherein the image used in the step of determining the inspection condition is obtained by reviewing the position on the sample determined to be reviewed.

3. The method of inspecting a sample as set forth in claim 2, wherein the reviewing is executed by the use of an optical inspection tool.

4. The method of inspecting a sample as set forth in claim 2, wherein the reviewing is executed by an inspection apparatus using a SEM.

5. A method of inspecting a sample, comprising the steps of:
   inspecting a sample under a plurality of inspection conditions and detecting a defect candidate with its position information;
   comparing the position information of each defect candidate detected under the plurality of inspection conditions;
   judging identity of the detected defect candidate under the plurality of inspection conditions to reduce the defect candidate to be reviewed by the use of information obtained at the comparing step;
   displaying an image of the identity judged defect candidate in a map form on a screen;
   determining a defect candidate to be inspected in detail out of the identity judged defect candidate;
   determining an inspection condition of the sample by the use of information of an image of the defect candidate which is determined to be inspected in detail at the defect candidate determining step; and
   inspecting other samples under the determined inspection condition.

6. The method of inspecting a sample as set forth in claim 5, wherein the image used in the step of determining the inspection condition is obtained by reviewing the position on the sample determined to be reviewed.

7. The method of inspecting a sample as set forth in claim 6, wherein the reviewing is executed by using an optical inspection tool.

8. The method of inspecting a sample as set forth in claim 6, wherein the reviewing is executed by an inspection apparatus using a SEM.

9. An apparatus for inspecting a sample, comprising:
   inspection means for inspecting a sample under plurality of inspection conditions and detecting a defect candidate;
   inspection condition setting means for setting the inspection condition of the inspection means;
   storage means for storing the position data of the defect candidate of on the sample, which is obtained by the inspection means by sequentially inspecting the sample under a plurality of inspection conditions set by the inspection condition setting means;
   checking means for checking identity of the defect candidate by comparing the position data of the defect candidate to be inspected in detail, the position data is detected under the plurality of inspection conditions to reduce a position to be inspected in detail and stored in the storage means;
   display means for displaying an image of the identity checked defect candidate in a map form on a screen; and
   inspection condition determining means for determining the inspection condition of the sample by the use of information of the image of the identity checked defect candidate and inputting the determined inspection condition to said inspection condition setting means.

10. The apparatus for inspecting a sample as set forth in claim 9, wherein the image of the checked identity of defect candidate used in the inspection condition determining means is obtained by reviewing the position on the sample determined to be reviewed with a reviewing tool.

11. The apparatus for inspecting a sample as set forth in claim 10, wherein the reviewing tool is an optical inspection apparatus.

12. The apparatus for inspecting a sample as set forth in claim 10, wherein the reviewing tool is an inspection apparatus using a SEM.

* * * * *